United States Patent [19]

Hayashi et al.

[11] 4,199,428
[45] Apr. 22, 1980

[54] SAMPLE FEEDER FOR USE IN AUTOMATIC ELECTROPHORESIS SYSTEM

[75] Inventors: Yoshiaka Hayashi; Kazuhiko Nakamura, both of Hachioji, Japan

[73] Assignee: Olympus Optical Co., Ltd., Tokyo, Japan

[21] Appl. No.: 25,931

[22] Filed: Apr. 2, 1979

[30] Foreign Application Priority Data

Apr. 27, 1978 [JP] Japan .............................. 53-55253[U]

[51] Int. Cl.² ...................... G01N 27/28; G01N 33/16
[52] U.S. Cl. ............................ 204/299 R; 204/180 G
[58] Field of Search .......... 204/180 R, 180 G, 180 S, 204/299 R, 300 R; 23/230 B; 424/12

[56] References Cited

U.S. PATENT DOCUMENTS

| | | | |
|---|---|---|---|
| 3,317,418 | 5/1967 | Zec ................................... | 204/299 R |
| 3,421,998 | 1/1969 | Yallen .............................. | 204/299 R |
| 3,428,547 | 2/1969 | Zec ................................... | 204/299 R |
| 3,616,387 | 10/1971 | Siebert et al. ...................... | 204/299 X |
| 3,839,183 | 10/1974 | Klein et al. ........................ | 204/299 |

*Primary Examiner*—Arthur C. Prescott
*Attorney, Agent, or Firm*—Ostrolenk, Faber, Gerb & Soffen

[57] ABSTRACT

A sample feeder for use in an electrophoresis system comprises a sample tray on which a plurality of the sample containers are placed in juxtaposition, and a carriage on which the sample tray is placed. The carriage is driven for movement, and individual sample containers on the sample tray are sequentially fed into alignment with a sample applicator of the electrophoresis system.

13 Claims, 10 Drawing Figures

SAMPLE FEEDER FOR USE IN AUTOMATIC ELECTROPHORESIS SYSTEM

BACKGROUND OF THE INVENTION

The invention relates to a sample feeder for use in an automatic electrophoresis system, and more particularly, to a feeder which is adapted to feed a plurality of samples to be examined into alignment with the sample applicator of an electrophoresis system.

As is well recognized, an automatic electrophoresis system may be used to examine the protein of blood serum in hospitals, for example. A sample bearing member in the form of a sheet of a material such as cellulose acetate is dampened with a buffering solution by means of a dampening roller before it is brought to a sample application position where blood serum, as a sample to be examined, is applied to it. The member with serum applied to it is then fed into an electrophoretic vessel which is then electrically energized to effect an electrophoretic process, which produces a fractionated pattern. Subsequently, the member is moved into a dyeing vessel where it is dyed, followed by decoloration and drying steps. Finally, the serum is examined photometrically by means of a densitometer, output data from which are recorded.

Figure 1:
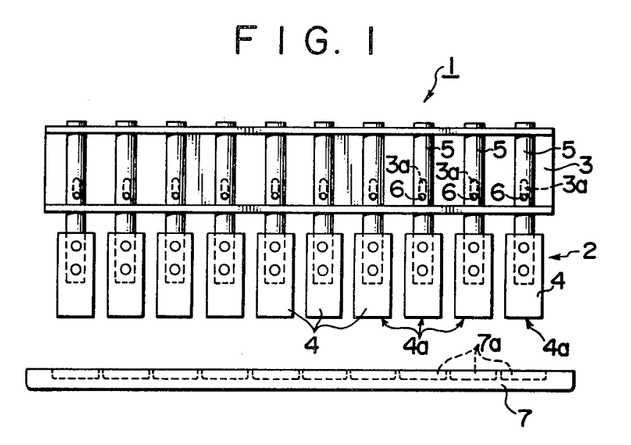
FIG. 1 is a front view of one exemplary sample applicator used in an electrophoresis system.

The serum is applied to the sample bearing member by means of an applicator as shown at 1 in FIG. 1. Specifically, the applicator 1 includes a plurality of application members 2 which are carried by a holding arm 3 at a regular spacing. Each application member 2 comprises a plate-shaped penpoint 4 having a surface 4a on its free end on which blood serum is deposited and which is fixed to the free end of a support shank 5. The shank 5 fixedly carries a laterally extending pin 6 which is engaged with an elongate slot 3a formed in the holding arm 3, thus allowing a limited vertical movement of the shank relative to the arm.

Figure 2:
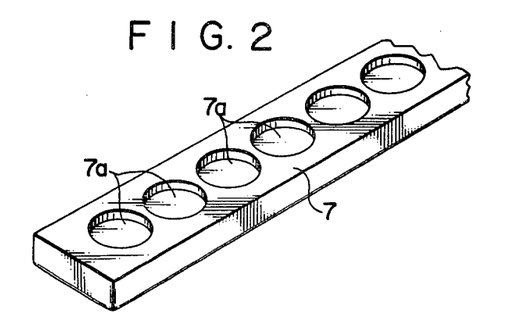
FIG. 2 is a perspective view of a sample container which is adapted to contain sample serums.
Figure 3:
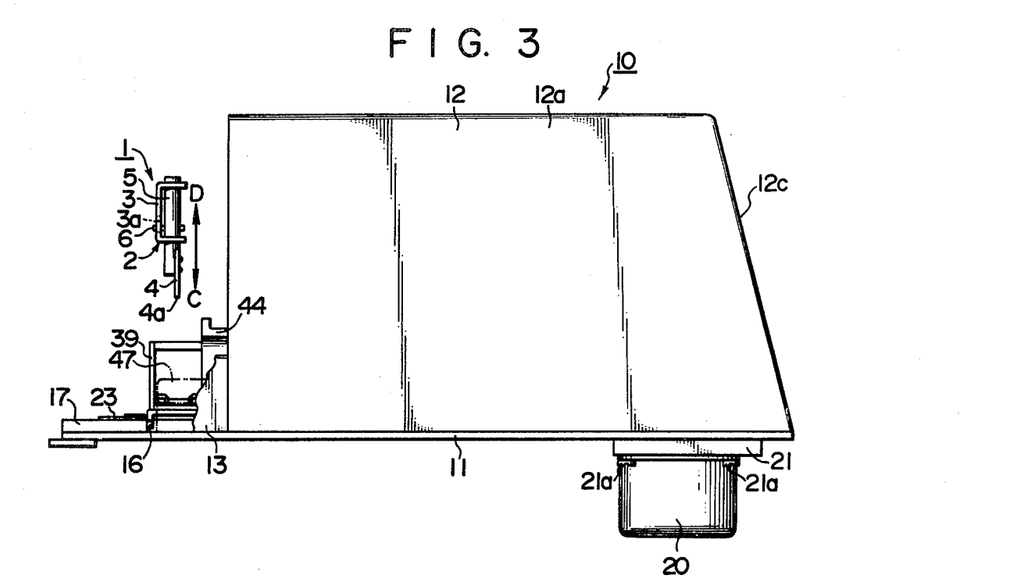
FIG. 3 is a schematic side elevation of the sample feeder according to one embodiment of the invention.

When blood serum is to be deposited on the bearing members by using the applicator 1, holding arm 3 is located over and moved down toward a sample container 7 having a plurality of dish-shaped recesses 7a each containing a different blood serum. The serum sample is deposited on the surface 4a of the penpoint 4. As illustrated in FIG. 2, the container 7 comprises an elongated, plate-shaped member having a plurality of dish-shaped recesses 7a formed in a row in its upper surface, regularly spaced and corresponding to the adjacent penpoints 4 of the applicator 1. After the penpoints 4 are immersed in the recesses 7a to allow blood serum to be deposited on the individual penpoints 4, the holding arm 3 is moved upward and is then moved over sample bearing members (not shown). The applicator is then moved down to cause individual penpoints 4 to abut corresponding bearing members, thus applying the blood serum samples to the latter.

An automatic electrophoresis system is capable of applying a number of blood serums to different bearing members automatically at one time. In addition, it automatically effects the fractionation, dyeing, decoloration and colorimetric quantitative determination for a plurality of serums in succession.

However, it will be noted that a plurality of sample containers 7 each containing samples to be tested must be initially prepared and then placed one by one, in the proper position relative to the applicator 1 in order that all the samples in all the containers 7 can be tested. In the prior art practice, this operation was performed manually. While other processing steps occur automatically in an automatic electrophoresis system, manual supply of samples by an operator results in reduced overall efficiency. Additionally, the manual operation is cumbersome. Thus, it will be apparent that there has been a need for automatic supply of samples.

SUMMARY OF THE INVENTION

In view of the foregoing, it is an object of the invention to provide a sample feeder for use in an automatic electrophoresis system, including a sample tray carrying a plurality of sample containers which is so placed on a carriage that a movement of the carriage permits samples from individual sample containers to automatically supplied to the application members.

It is another object of the invention to provide a sample feeder of the type described which prevents samples contained in those sample containers which are disposed on the sample tray from drying while they await deposition on the applicator during their standby.

In accordance with the invention, a plurality of sample containers containing sample serums are juxtaposed on a sample tray which is in turn placed on a carriage. The carriage can be electrically driven to align a number of samples with sample application members in a sequential manner. This avoids the necessity of a manual operation by an operator to bring each sample container into alignment with the applicator, thus contributing to a full automation of an electrophoresis system. Manual operation can be minimized to improve the overall efficiency, by providing a plurality of sample trays, on each of which sample containers are disposed. The only manual operation required will be that of placing each sample tray on the carriage. This also avoids an inadvertent manual operation.

In accordance with another aspect of the invention, a cover means is provided for preventing the desiccation of samples. This means cover the top of sample containers which are disposed on the sample tray during their standby period. In this manner, the samples can be maintained in good condition for examination.

DESCRIPTION OF PREFERRED EMBODIMENT

Figure 4:
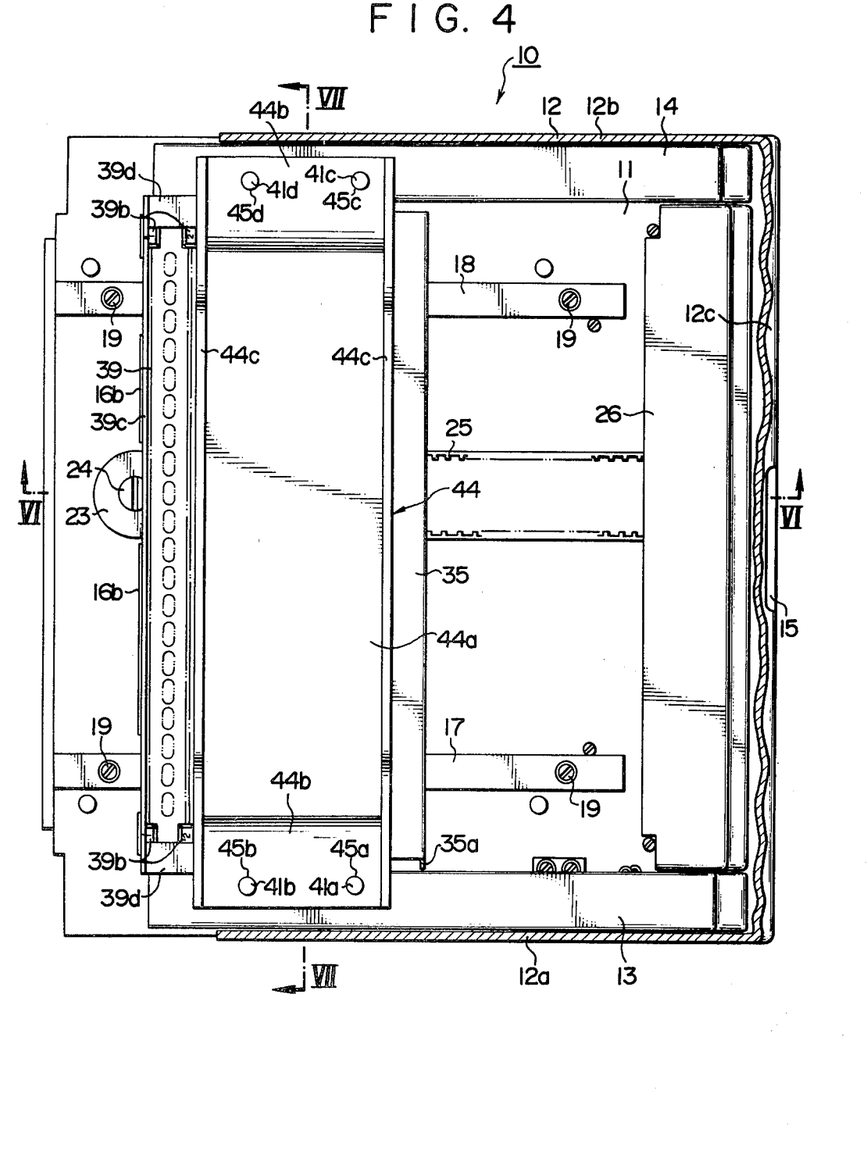
FIG. 4 is a plan view of the sample feeder shown in FIG. 3, with the top cover being removed to show the internal construction.
Figure 5:
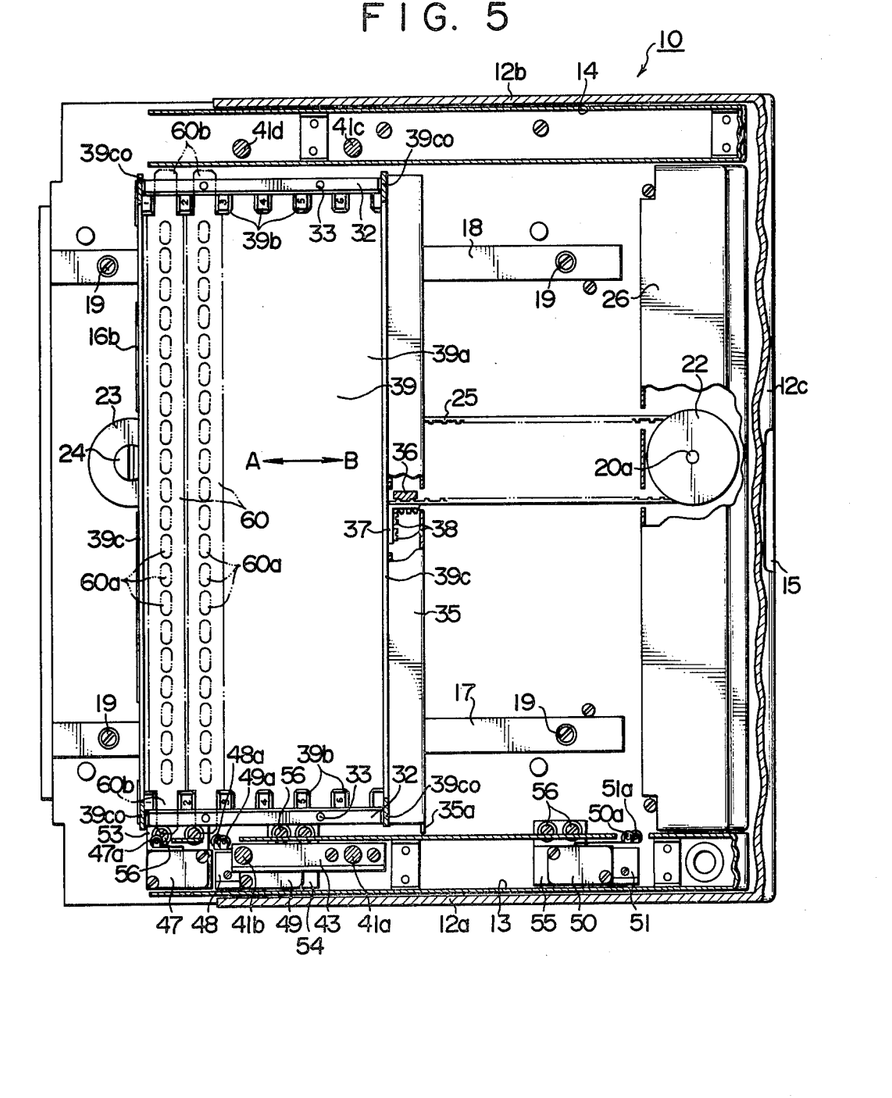
FIG. 5 is a plan view of the sample feeder, illustrating the specific detail of cover means which prevent a drying of samples.
Figure 10:
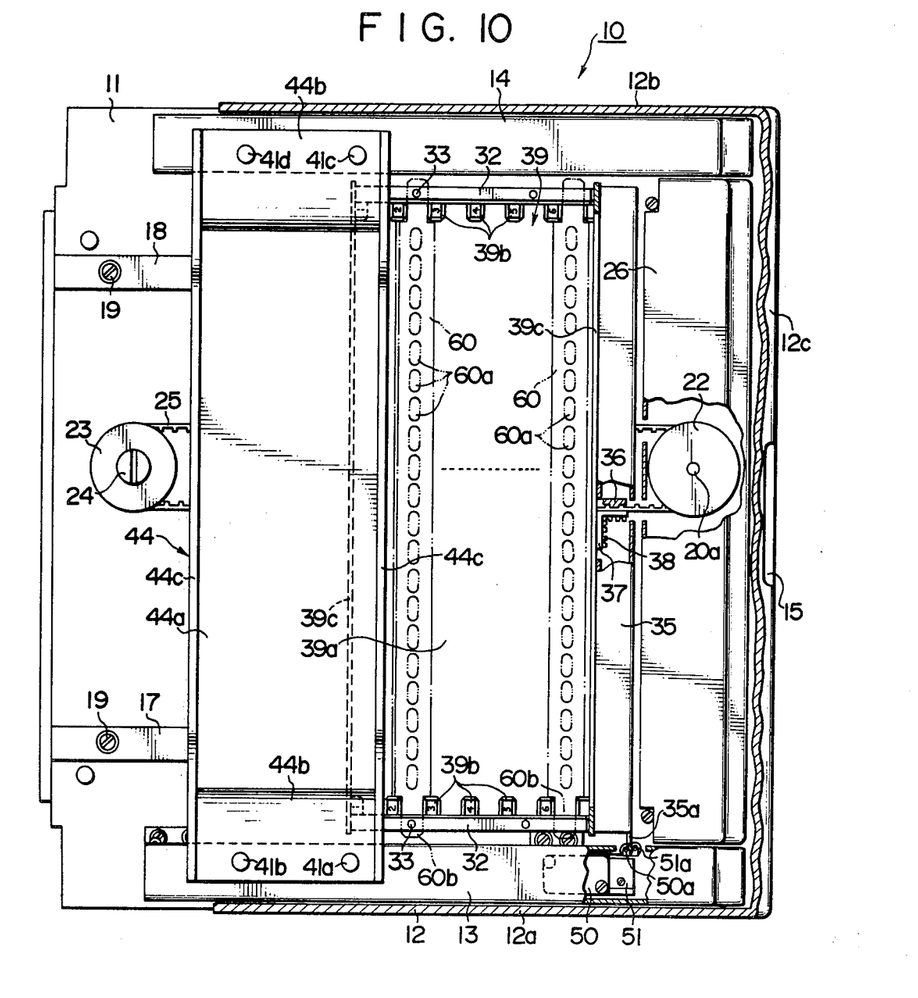
FIG. 10 is a plan view illustrating the starting condition of the sample feeder.

Referring to FIGS. 3 to 7, there is shown a sample feeder 10 which is constructed in accordance with one embodiment of the invention. The feeder 10 comprises a base 11 on which a carriage 16 is disposed and which is normally covered by an enclosure 12 which is detachably mounted on the base 11. At one end which is located near a serum applicator 1 (see FIG. 3), the enclosure 12 is open to permit a sample container to be moved into position below the applicator 1. It is to be understood that in the illustration of FIGS. 3, 4, 5 and 10, the right-hand side represents the front side and the left-hand side the rear side of the feeder 10. In a corresponding manner, the illustration in FIGS. 4, 5 and 10 is such that the upper side of the figure represents the right-hand side and the lower side the left-hand side of the feeder 10. The enclosure 12 includes a front plate 12c of a pair of sideplates 12a, 12b, the inner wall of which bears against respective outer walls of a pair of channel-shaped members 13, 14 which are mounted on the base 1 along its opposite sides. The front plate 12c is centrally formed with a notch 15 in the bottom thereof to facilitate its manual removal.

A pair of guiderails 17, 18 which have an inverted L-shaped cross section are fixedly mounted on the base 11 by means of screws 19 in order to permit movement of the carriage 16 in the back-and-forth direction, namely, in the directions indicated by arrows A, B (see FIG. 5). Adjacent to the front end of the base 11, a motor 20, representing a drive source for moving the carriage 16, is secured to the underside of the base by set screws 21a, with a mount 21 interposed therebetween. The motor has a drive shaft 20a which extends through the base 11 and which fixedly carries a first pulley 22 (see FIGS. 5 and 6) on its free end. A second pulley 23 is rotatably mounted on a shaft 24 which is fixedly mounted on the base 11 toward the rear end of the base 11 (see FIGS. 4, 5, 6). A timing belt 25 extends around the pair of pulleys 22, 23. It will be noted that the first pulley 22 is protected from exposure to the exterior by a cover member 26 which is elongate transversely to and is mounted on the base 11.

Figure 7:
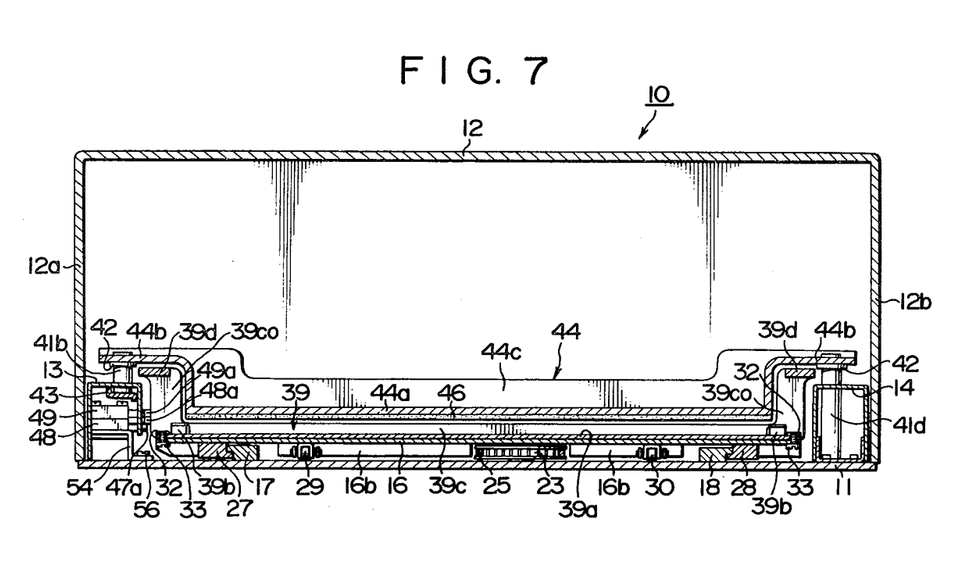
FIG. 7 is a cross section taken along the line VII—VII shown in FIG. 4.
Figure 8:
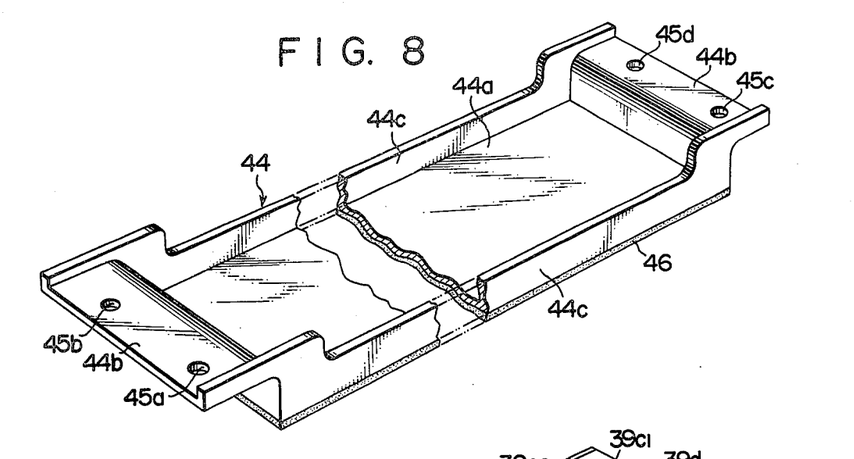
FIG. 8 is a perspective view of cover means which prevents the drying out of samples.
Figure 9:
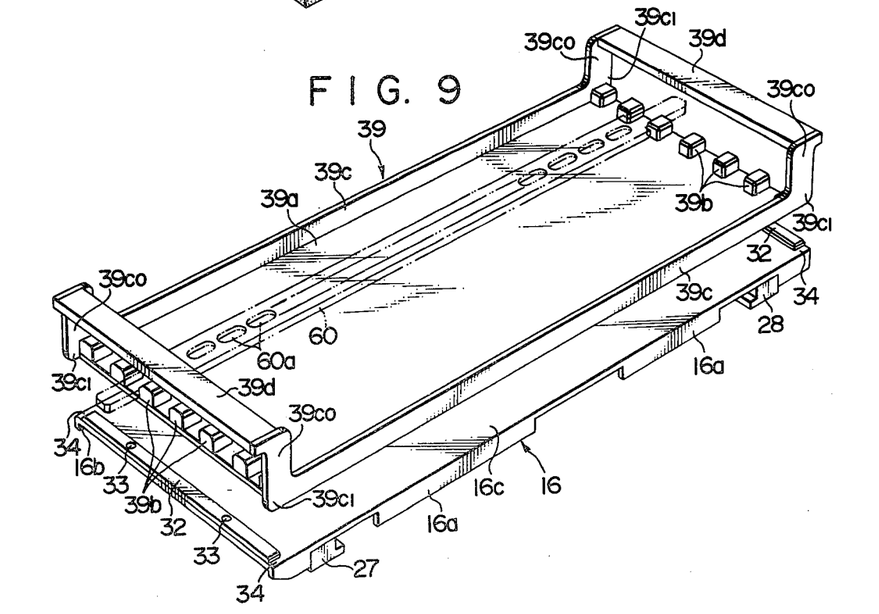
FIG. 9 is a perspective view of a sample tray and an associated carriage which are used in the sample feeder of the invention.

As shown in FIGS. 7 and 9, the carriage 16 is in the form of a plate which is elongate transversely to the base, and fixedly carries a pair of L-shaped guide members 27, 28 on its underside adjacent to the opposite lateral sides, which slidably engage the guide rails 17, 18, respectively. The carriage 16 has front and rear downwardly depending edges 16a, 16b, which are notched to avoid interference with the timing belt 25 and guide rails 17, 18. A pair of guide rollers 29, 30 (see FIG. 7) are rotatably mounted on the underside of the carriage 16 intermediate the pair of depending edges 16a, 16b for abutment against the base 11 in order to support the carriage 16. The carriage 16 also includes a flat upper surface 16c, the opposite lateral edges of which are provided with positioning members 32 which are used to position a sample tray 39 immovably on the carriage 16. The positioning members 32 are elongate and plate-shaped, with their length being less than the length of the carriage 16. Steps or shoulders 34 are defined between the front and rear ends of the members 32 and the upper surface 16c of the carriage 16.

Figure 6:
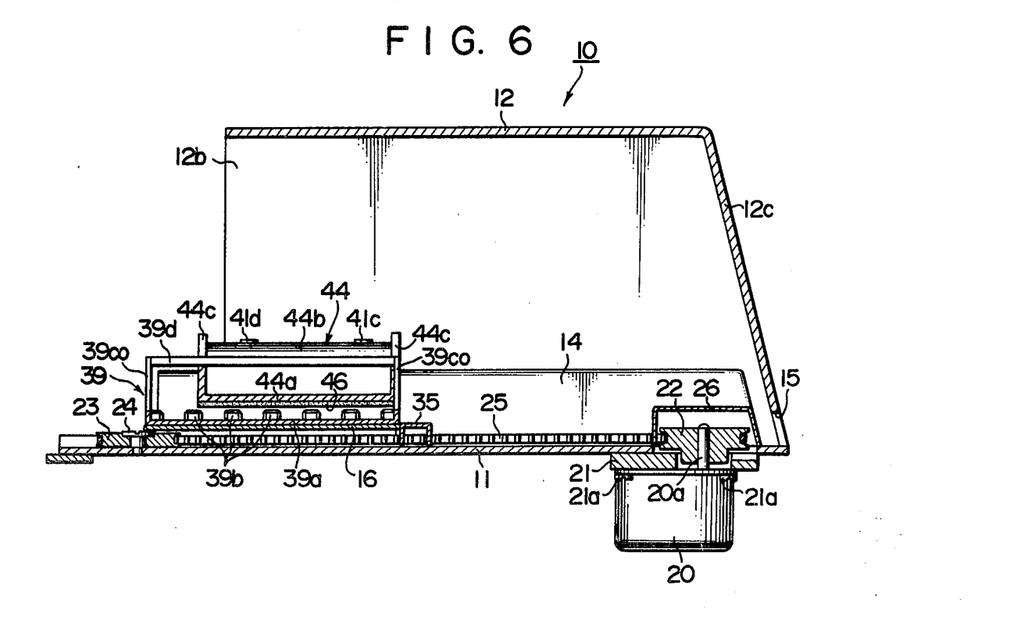
FIG. 6 is a cross section taken along the line VI—VI shown in FIG. 4.

In FIGS. 4 to 6, a channel-shaped cover 35 is fixed to the front edge 16a, and is internally provided with a belt abutment 36 substantially at its midpoint. The belt abutment 36 and an L-shaped fastener 37, which is secured to the edge 16a by screw 38, hold part of the timing belt 25 between them, thereby connecting the belt 25 to the carriage 16. Thus, as the belt 25 runs, the carriage 16 moves in the direction of arrow A or B. The end of the front sidewall of cover 35 near the channel member 13 is formed with a lug 35a, which is adapted to open or close control switches 48 to 51, as will be described later.

As shown in FIG. 9, the sample tray 39 which is disposed on the carriage 16 comprises a bottomplate 39a which substantially conforms to the upper surface 16c of the carriage 16, and a pair of upright sideplates 39c which extend the front and rear edges of the bottomplate 39a. Along the lateral edges of the bottomplate 39a, a plurality of equally spaced spacing pieces 39b, which are seven in number in the example shown, are disposed. At each end, each respective sideplate 39c is formed with an extension 39c0 having an inverted L-configuration, and hand bars 39d extend along the sides of the tray 39 between to these extensions 39c0, to which they are secured. The lower ends of extensions 39c0 are formed with projections 39c1 which are adapted to engage the individual steps 34 of the carriage 16.

The bottomplate 39a has a length which substantially coincides with the distance between the pair of positioning members 32, as measured between their opposite inner end faces. The bottomplate 39a has a width which is equal to that of either positioning member 32. The extensions 39c1 from the front and rear sideplates 39c engage the steps 34 so as to bear against the front and rear end faces of the positioning members 32. Consequently, when the tray 39 is properly placed on the carriage 16, the lateral end faces of the bottomplate 39a bear against the inner end faces of the positioning members 32 while the inner side of the extensions 39c1 of the both sideplates 39c bear against the front and rear end faces of the positioning members 32, thus permitting integral movement of the tray 39 with the carriage 16 while avoiding any relative displacement of the tray 39d of the carriage 16 in longitudinal or transverse direction.

Pairs of stanchions 41a, 41b and 41c, 41d are fixedly mounted on the base 11 toward its rear end, and vertically extend through each channel member 13, 14 as illustrated in FIGS. 4, 5 and 7. One pair of stanchions 41a, 41b are fixedly mounted on an intermediate, L-shaped fastener 43 secured to the base 11 while the other pair of stanchions 41c, 41d are directly mounted on the base 11. These stanchions have flanges 42 (see FIG. 7) level with each other which are adapted to receive cover means 44 thereon, which serves to prevent the drying out of samples, as will be described below.

Cover means 44 comprises a tray-shaped plate member as indicated in FIGS. 4, 6, 7 and 8. It includes a bottomplate 44a having a width which is less than the width of tray 39 by an amount corresponding to the width of a sample container 60 to be described later and having a length which corresponds to the distance between transversely opposite spacing pieces 39b. The opposite end portions of the bottomplate 44a are folded into L-configuration so as to form horizontally extending grip portions 44b. The front and rear edges of the bottomplate 44a are bent upward to form sideplates 44c. The grip portions 44b are formed with holes 45a, 45b, 45c, 45d, which are adapted to fit over the stanchions 41a to 41d. When these holes are engaged with the stanchions 41a to 41d, one of the grip portions 44b rests on the flanges 42 formed on stanchions 41a, 41b while the other grip portion 44b rests on the other flanges 42, thus holding cover means 44 at a given elevation above the tray 39.

This elevation is chosen such that a sheet liner 46 applied to the underside of the bottomplate 44a does not contact, but is closely spaced from the top of sample container 60 which may be placed on the tray 39. The liner is impregnated with water so as to be kept damp, thus serving to prevent the drying out of samples which are located below it.

Referring to FIGS. 5 and 7, the channel member 13 internally houses drive control means associated with the carriage 16. It comprises a plurality of microswitches 47 to 51, which have their actuators formed by contact rollers 47a to 51a, which are aligned with each other on a line which extends parallel to the direction of movement of the carriage 16. Microswitch 47 is used to stop the carriage, and is mounted on the base 11 toward its rear end and thus close to the applicator 1, by means of L-shaped bracket 53. Microswitches 48, 49 are used to return the carriage, and are mounted on the base 11 forward of the microswitch 47 by L-shaped bracket 54, which their contact rollers 48a, 49a slightly offset from each other in the longitudinal direction. Microswitches 50, 51 are used to stop the return movement of the carriage, and are mounted on the base 11 toward its front end by L-shaped fastener 55, with their contact rollers 50a, 51a again slightly offset from each other in the longitudinal direction. It will be noted that brackets 53, 54, 55 are mounted on the base 11 by set screws 56.

In operation, before operating the sample feeder 10, a plurality of sample containers 60 are disposed on the tray 39, at a point remote from the feeder 10. As shown in FIGS. 5, 9 and 10, each sample container 60 is formed with a series of longitudinally aligned, sample containing recesses 60a, which are twenty in number, and which are spaced apart by a distance corresponding to the distance between adjacent penpoints 4 of the applicator 1 (see FIGS. 1 and 3). The ends of the container 60 have tongues 60b so that they can be received between a pair of adjacent distance pieces 39b fixedly mounted on the tray 39. It is to be noted that when arranged in this manner, these tongues 60b project beyond the opposite lateral sides of the tray 39. Since there are seven spacing pieces 39b disposed along the opposite sides of the tray 39, it is possible to plate a total of six containers 60, or a total of 120 samples, thereon.

The enclosure 12 is then removed from the base 11, and the carriage 16 is moved to its forward position shown in FIG. 10. The tray 39 on which the containers 60 are placed is then disposed on the carriage 16 by holding the grip portions 39b with both hands. The tray 39 is disposed on the carriage in a manner such that the extensions 39c1 from the sideplates 39c engage the steps 34 defined by positioning members 32 so that it can be moved integrally with the carriage 16. This condition is illustrated in FIG. 10. Cover means 44 is fitted over stanchions 41a to 41d, and the enclosure 12 is then replaced on the base 11. The channel members 13, 14 assure that the enclosure 12 is mounted in position on the base 11 securely. Subsequently, a power switch may be turned on to energize the motor 20. Thereupon the pulley 22 begins to rotate clockwise, driving timing belt 25 around pulleys 22, 23. Because the carriage 16 is connected with the belt 25, it begins to move rearwardly or in the direction of arrow A together with the tray 39 disposed thereon. When the carriage 16 reaches the position shown in FIG. 4, the rearmost container 60 disposed on the tray 39, or foremost as viewed in the direction of arrow A, has its end 60b, which is located opposite to the channel member 13, brought into abutment against contact roller 47a of microswitch 47, thus actuating it. Thereupon, the motor 20 is deenergized, bringing the carriage 16 to a stop. At this initial stop position of the carriage 16, the individual penpoints 4 of the applicator 1 are aligned with corresponding recesses 60a formed in the first container 60.

When the carriage 16 is stopped in this manner, the applicator 1 may be operated to move application members 2 downward or in a direction indicated by arrow C (see FIG. 3), thus applying sample serums contained in the individual recesses 60a of the container 60 to the corresponding surfaces 4a of the penpoints 4.

It is to be noted that at this stop position of the carriage 16, only the first container 60 is exposed, while the remaining five containers 60 are covered by cover means 44. As mentioned previously, the sheet liner 46 is impregnated with water and thus is moistened, preventing samples contained in the fine containers 60 in standby condition from drying.

When sample serums are applied to the individual penpoints 4, the application members 2 are raised in a direction indicated by arrow D (see FIG. 3), and the deposited sample serums on the penpoints 4 can be applied to serum bearing members (not shown). (As mentioned initially, the samples applied to these bearing members are subjected to an electrophoretic process in order to form a fractionated pattern.) In the meantime, the motor 20 is energized again to cause a further movement of the carriage 16 in the direction of arrow A. The end 60b of the second container 60 bears against the contact roller 47a to actuate microswitch 47, whereupon the motor 20 is deenergized again. This stops the carriage 16 for the second time. In this instance, the second container 60 is located in alignment with the applicator 1.

In this manner, the six containers 60 disposed on the tray 39 are sequentially brought into alignment with the applicator 1 for depositing the samples contained in the container 60 on the penpoints 4. As the motor 20 is energized again to cause a further movement of the carriage 16 in the direction of arrow A after the last container 60 has actuated microswitch 47 and after the deposition of its samples on the applicator 1 has been completed, projection 35a laterally extending from the cover 35, which is fixed to the carriage 16, bears against contact roller 49a, thus actuating microswitch 49. This deenergizes the motor 20 to stop the carriage 16. In the event the microswitch 49 fails to be operated for some reason, the safety microswitch 48 is actuated to deenergize the motor 20 when the carriage 16 reaches a slightly more forwardly advanced position. The movement of the carriage 16 is stopped in response to the actuation of the microswitch 49, and the motor 20 is then reversed to initiate a returning movement of the carriage 16 in the direction of arrow B. When the projection 35a bears against contact roller 50a to actuate microswitch 50, the motor 20 is deenergized, whereupon the carriage 16 resumes its initial position (shown in FIG. 10) and stops. In the event that the microswitch 50 fails to be actuated for some reason, the safety microswitch 51 is actuated instead to stop the motor 20. When the carriage 16 reaches a slightly further retracted position. When the carriage 16 is stopped in response to the actuation of microswitch 50, it resumes its initial position shown in FIG. 10.

Subsequently the tray 39 can be removed from the carriage 16 and replaced by another tray 39 having fresh sample containers 60 disposed thereon. The described procedure is repeated again with this second tray 39.

In the sample feeder 10 described above, it is also possible to return the carriage 16 to its initial position from an intermediate position. This may be desirable where an error in the order of disposition of sample serums is found or in order to permit a manual application of selected samples to the applicator which need an immediate determination. It is accomplished by reversing the motor 20 to return the carriage 16 to its initial position, where the error can be corrected or the emergency samples can be loaded.

When the individual samples contained in a single container 60 are deposited on the individual penpoints 4 using the sample feeder 10, the samples are then applied to the sample bearing members, which are then fed to an electrophoretic box which is then energized to form a fractionated pattern. The deposition of samples from the next container 60 does not take place until the electrophoretic process which is conducted on the initial samples is completed. Thus, there is a certain length of time between the deposition of samples from successive sample containers. The time which passes from the deposition of samples from the initial container and the deposition of samples from the last container will be quite long, and if the samples are left open in their sample containers, they will be dried up, with an adverse influence upon the determination. Cover means 44 which is provided in the present invention prevents this from occurring. Specifically, when cover means 44 having the sheet member 46 on its underside impregnated with water is placed over the stanchions 41a to 41d, samples for which the applicator 1 is not yet ready are covered by the moistened sheet member 46 and thus are protected from drying. It is found that the sheet member 46 may be moistened immediately before the feeder 10 starts its operation. However, the bottomplate of cover means 44 may be formed with a multiplicity of small apertures to permit permeation of water, initially supplied over the tray-shaped area of the bottomplate, to the sheet member 46 therethrough, thus maintaining the sheet member 46 maintained moistened for a prolonged period of time. Any other means may be used to maintain the sheet member 46 moistened.

Although a preferred embodiment of the invention has been described, many modifications and variations thereof will now be apparent to one skilled in the art, and it is accordingly preferred that the scope of the invention be limited not by the details of the embodiment described above but only by the appended claims.

What is claimed is:

1. A sample feeder for use in an automatic electrophoresis system, comprising:
   (a) a plurality of sample holders each adapted to hold a sample to be tested by said electrophoresis system;
   (b) carriage means supporting said sample holders at spaced locations thereon; and
   (c) means for moving said carriage relative to a sample application position, said means moving said carriage in such a manner that each of said sample holders is successively moved into said sample application position and retained in said position for a finite period of time in order that a sample may be taken therefrom.

2. A sample feeder according to claim 1 wherein said moving means comprises:
   (a) drive means for moving said carriage; and
   (b) control means for controlling the operation of said carriage in such a manner that said carriage is:
      (1) moved from a first position to a second position in a stepped fashion wherein said carriage is stopped at each of a plurality of intermediate positions when moving from said first to said second positions of said intermediate positions positioning a different one of said sample holders in said sample application position; and
      (2) moved from said second back to said first position.

3. A sample feeder according to claim 2, wherein said control means causes said drive means to move from said second to said first position in a continuous manner.

4. A sample feeder according to claim 1, wherein said carriage means comprises:
   a carriage moveable relative to said sample application position; and
   a sample tray supported by said carriage and moveable therewith, said sample tray supporting said sample holders.

5. A sample feeder according to claim 2, further comprising cover means which is so located over the path of said carriage that when said carriage is in one of said intermediate positions, such of said sample containers as have not yet been brought into said sample application position are covered by said cover means.

6. A sample feeder according to claim 5, wherein said cover means has a lower surface to which is secured a sheet of a material capable of absorbing and retaining water, whereby samples contained in such of said sample holders as are under said cover means are protected from desiccation.

7. A sample feeder according to claim 1, further comprising:
   a base;
   a guide rail disposed on said base, for restricting motion of said carriage to motion in either direction along one axis:
   a first pulley, rotatably mounted on said base;
   a second pulley, connected to and drivable by said drive means;
   a belt connected to said first and second pulleys and to said carriage, for translating power for said drive means into rectilinear motion of said carriage.

8. A sample feeder according to claim 1, in which said carriage has a base, and has a roller rotatably mounted on it such that said carriage can be moved on said base by rolling.

9. A sample feeder according to claim 2, in which said control means comprises a stop switch, a carriage return switch, and a return stop switch; said switches being disposed on said base in a line parallel to the direction of movement of said carriage.

10. A sample feeder according to claim 9, in which said sample tray has a side wall; each said sample container having a portion that projects through and beyond said side wall of said sample tray; said stop switch being actuated by said projecting portion of each of said containers in sequence as said carriage moves from said first to said rewind position, and operating to deenergize said drive means.

11. A sample feeder according to claim 9, in which said return switch is actuated by a projection extending from said carriage, and is so located that it is actuated to stop said carriage and reverse said drive means when said carriage reaches said second position.

12. A sample feeder according to claim 9, in which said return stop switch is actuated by a projection extending from said carriage, and is located so as to be actuated to deenergize said drive means when said carriage has reached said first position.

13. A sample feeder according to claim 9, in which all of said switches are microswitches.

* * * * *